US012805877B2

(12) United States Patent
Zhang et al.

(10) Patent No.: US 12,805,877 B2
(45) Date of Patent: Nov. 24, 2026

(54) THREE-ARM CLIP

(71) Applicants: MICRO-TECH (NANJING) CO., LTD., Jiangsu (CN); Qiang Zhang, Guangdong (CN)

(72) Inventors: Qiang Zhang, Guangdong (CN); Hongyan Jin, Jiangsu (CN); Xiaojun Ma, Jiangsu (CN)

(73) Assignees: MICRO-TECH (NANJING) CO., LTD., Jiangsu (CN); Qiang Zhang, Guangdong (CN)

( * ) Notice: Subject to any disclaimer, the term of this patent is extended or adjusted under 35 U.S.C. 154(b) by 132 days.

(21) Appl. No.: 18/746,788

(22) Filed: Jun. 18, 2024

(65) Prior Publication Data

US 2024/0415517 A1 Dec. 19, 2024

(30) Foreign Application Priority Data

Jun. 19, 2023 (CN) ........................ 202321576249.8

(51) Int. Cl.
*A61B 17/122* (2006.01)

(52) U.S. Cl.
CPC ................................ *A61B 17/122* (2013.01)

(58) Field of Classification Search
CPC ....... A61B 17/122; A61B 17/04; A61B 17/12; A61B 17/0469; A61B 17/0483; A61B 17/0487; A61B 17/0464; A61B 17/068; A61B 17/08; A61B 17/083; A61B 2017/2808; A61B 2017/0641; A61B 2017/0643; A61B 2017/0644; A61B 2017/1125
See application file for complete search history.

(56) References Cited

U.S. PATENT DOCUMENTS

2023/0263533 A1* 8/2023 Shindo .............. A61B 17/1227
606/151

* cited by examiner

*Primary Examiner* — Brooke Labranche
*Assistant Examiner* — Rachel L Geiger
(74) *Attorney, Agent, or Firm* — BCF LLP

(57) ABSTRACT

A three-arm clip is provided, which relates to the technical field of medical devices. By providing self-locking slots and realizing self-locking between movable arms and a fixed portion in cooperation with sliding slot pins, a snap-fitting structure such as a limiting elastic sheet may not be added to the movable arms, so that the three-arm clip has a reduced outer diameter, and may pass through an endoscope with a small working channel.

13 Claims, 7 Drawing Sheets

THREE-ARM CLIP

CROSS-REFERENCE TO RELATED APPLICATIONS

The present disclosure claims priority to the Chinese patent application with the filing No. 202321576249.8, filed with the Chinese Patent Office on Jun. 19, 2023, and entitled "THREE-ARM CLIP", all the contents of which are incorporated herein by reference in entirety.

TECHNICAL FIELD

The present disclosure relates to the technical field of medical devices, and particularly to a three-arm clip.

BACKGROUND ART

With the development of endoscopic technologies, endoscopic minimally invasive surgery has received more and more attention, and has advantages of small wound, quick postoperative recovery and low medical costs. Defect/wound surface closure is a quite common problem in minimally invasive surgery, and is also a technical challenge. Efficient closure of a defect wound surface is conducive to promotion and popularization of minimally invasive technologies, and is more beneficial to reducing occurrence of complications of minimally invasive surgery.

At present, a three-arm clip for defect closure under an endoscope attracts much attention. Such endoclip, which can effectively close a large-size wound surface and a wound surface difficult to be closed, clamps tissues on one side of an edge of a wound surface, and pulls them to tissues on the other side close to the edge of the wound surface, so as to close the tissues on the two sides of the wound surface together, thereby achieving the purpose of closing the wound surface.

For the prior art, the structure of the three-arm clip mostly realizes locking of the endoclip through a mechanical stopper, such as an elastic sheet or a bulge. Such structural locking is firm and reliable. However, the structure is precise and complex, so that a device has a large overall outer diameter, and can hardly pass through the endoscope with a small working channel, for example, endoscope with a 2.8 mm working channel or a channel less than 3.2 mm, which limits options for endoscope use.

SUMMARY

The present disclosure aims at providing a three-arm clip, so as to alleviate the technical problem of the complex locking structure of the existing three-arm clip.

The present disclosure provides a three-arm clip, including a clamping component, wherein the clamping component includes a fixed portion and two movable arms rotationally connected to the fixed portion, and the movable arms have an open state, a closed state and a self-locking state;

the clamping component further includes two sliding slot pins, each of the movable arms is provided with a first sliding slot, the fixed portion is provided with a guiding slot extending in a distal-proximal direction, wherein when the movable arms are in the closed state, an extending direction of the first sliding slot is inclined relative to an extending direction of the guiding slot; each of the sliding slot pins is provided in the first sliding slot and the guiding slot, and along the guiding slot, by driving the sliding slot pins, the movable arms can be driven to be switched between the closed state and the open state; and each of the movable arms is provided with a self-locking slot, a distal end of the self-locking slot communicates with a proximal end of the first sliding slot; and along the guiding slot, when each of the sliding slot pins slides from the proximal end of the first sliding slot to a proximal end of the self-locking slot, the movable arm is switched from the closed state to the self-locking state.

Further, when each of the movable arms is in the self-locking state, an axis b of the sliding slot pin is located on a central plane of the guiding slot, wherein a central line of the guiding slot is located on the central plane, and an opening-closing direction of each of the movable arms is perpendicular to the central plane;

when each of the movable arms is in the self-locking state, the distal midpoint a of the self-locking slot is located on the central plane; or a distal midpoint a of the self-locking slot and a distal midpoint c of the first sliding slot are located on two opposite sides of the central plane, respectively; or the distal midpoint a of the self-locking slot and the distal midpoint c of the first sliding slot are located on the same side of the central plane, and an included angle β between a connecting line between the distal midpoint a of the self-locking slot and the axis b of the sliding slot pin and the central plane is within a preset self-locking angle range; and each of the sliding slot pins is located in the self-locking slot and makes the movable arms maintain the self-locking state relative to the fixed portion through the guiding slot.

Further, when each of the movable arms is in the self-locking state, the distal midpoint a of the self-locking slot and the distal midpoint c of the first sliding slot are located on the same side of the central plane, and the included angle β between the connecting line between the distal midpoint a of the self-locking slot and the axis b of the sliding slot pin and the central plane is within the preset self-locking angle range; and a value range of the preset self-locking angle β is 0-8°.

Further, the fixed portion includes a fixed arm extending in the distal-proximal direction, and each of the movable arms is rotationally connected to the fixed arm; and the guiding slot includes a second sliding slot provided on the fixed arm, wherein the second sliding slot runs through front and back surfaces of the fixed arm, and tail ends of the sliding slot pins corresponding to the two movable arms extend into the second sliding slot from the front and back surfaces of the fixed arm.

Further, the fixed portion includes a fixed arm extending in the distal-proximal direction, and each of the movable arms is rotationally connected to the fixed arm;

the fixed portion further includes two covers extending from near to far, the two covers are provided on the front and back surfaces of the fixed arm and cover at least part of the two movable arms on the front and back surfaces of the fixed arm; and the guiding slot includes a third sliding slot provided on a surface of each of the covers facing the fixed arm, and a top end of each of the sliding slot pins is connected slidably in the third sliding slot.

Further, each of the sliding slot pins is provided with a cap on a top portion, and the cap is located in the third sliding slot; and the cap has a first guiding surface and a second guiding surface on two opposite sides, and the first guiding surface and the second guiding surface are respectively in sliding contact with two opposite slot walls of the third sliding slot.

Further, the fixed portion includes a fixed arm extending in the distal-proximal direction, the fixed arm is provided with shafts, and the movable arms are rotationally connected to the fixed arm through the shafts;

the three-arm clip further includes releasing members, wherein each of the releasing members is detachably connected to the sliding slot pin, and each of the releasing members is capable of driving the sliding slot pin to move along the guiding slot, so that the sliding slot pin moves in the first sliding slot and the self-locking slot; and each of the shafts is located outside a movement path of the releasing member.

Further, the fixed portion includes a fixed arm extending in the distal-proximal direction, the fixed arm is provided with shafts, and each of the movable arms is provided with a hole connected with the shaft, and each of the movable arms is rotationally connected to the fixed arm through the shaft;

the three-arm clip further includes releasing members, wherein each of the releasing members is detachably connected to the sliding slot pin, and each of the releasing members is capable of driving the sliding slot pin to move along the guiding slot, so that the sliding slot pin moves in the first sliding slot and the self-locking slot; and a depth of the hole is greater than or equal to a height of the shaft, so that a top end of the shaft is lower than or flush with an outer side surface of the movable arm, so as to prevent the shaft from interfering with movement of the releasing member.

Further, at least part of projection of profile of a motion path of each of the releasing members towards the movable arm falls within the hole.

Further, when the three-arm clip is in the closed state, a value range of a maximum outer diameter thereof is 2.3 mm-2.9 mm.

Further, the farthest end of the movement path of each of the releasing members goes beyond a position where the shaft is located.

The present disclosure at least has the following advantages or beneficial effects:

By pushing the sliding slot pins distally, the sliding slot pins can be moved distally along the guiding slot. During the movement, the sliding slot pins push the inclined first sliding slots, so as to drive the movable arms to rotate relative to the fixed portion, and then the two movable arms are turned to the open state. On the contrary, by pushing the sliding slot pins proximally, the two movable arms may be turned to the closed state. When the two movable arms are completely turned to the closed state, the sliding slot pins are located at the proximal ends of the first sliding slots, and when pushing the sliding slot pins proximally again, the sliding slot pins may enter the self-locking slots, and the sliding slot pins located in the self-locking slots act with the guiding slot, so as to form the self-locking. Without external force intervention, the movable arms cannot be spread open solely by an expansion force of tissues clamped by the distal ends of the movable arms. In the present solution, by providing the self-locking slots and realizing the self-locking between the movable arms and the fixed portion in cooperation with the sliding slot pins, a snap-fitting structure such as a limiting elastic sheet may not be added to the movable arms, so that the three-arm clip has a reduced outer diameter, and may pass through an endoscope with a small working channel. Moreover, the structure is simplified and optimized, and difficulty of processing technology is reduced, so that production and quality costs are reduced, and good technology is popularized and applied.

BRIEF DESCRIPTION OF DRAWINGS

In order to more clearly illustrate the technical solutions in the embodiments of the present disclosure or the prior art, the drawings that need to be used in the description of the embodiments or the prior art will be briefly introduced below. Obviously, the drawings in the following description show some embodiments of the present disclosure, and those ordinarily skilled in the art also could obtain other drawings according to these drawings without using any inventive efforts.

REFERENCE SIGNS

Figure 1:
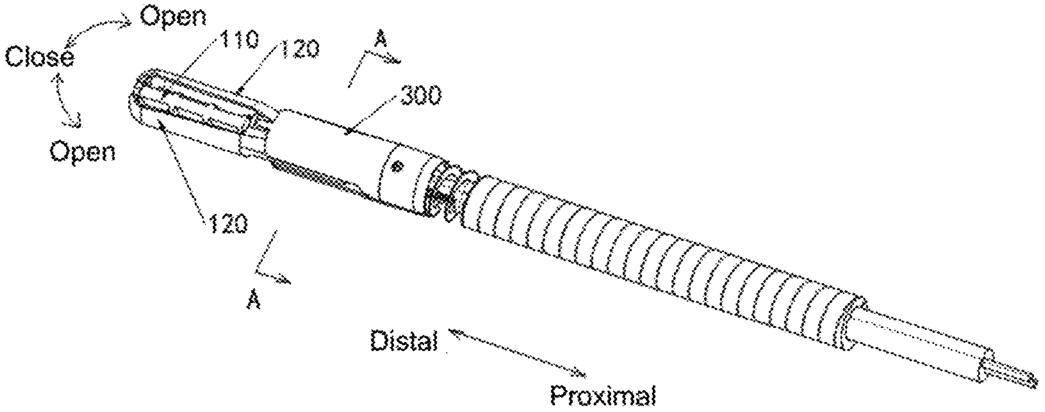
FIG. 1 is a schematic diagram of a three-arm clip provided in Embodiment 1 of the present disclosure.

110—fixed arm; 111—second sliding slot; 120—movable arm; 121—first sliding slot; 122—self-locking slot;

200—shaft;

300—cover; 310—third sliding slot;

400—releasing member; 500—sliding slot pin; 510—cap; 600—guiding slot.

DETAILED DESCRIPTION OF EMBODIMENTS

In order to make objectives, technical solutions and advantages of the embodiments of the present disclosure clearer, the technical solutions in the embodiments of the present disclosure will be described clearly and completely below in conjunction with the drawings in the embodiments of the present disclosure. Obviously, some but not all embodiments of the present disclosure are described. Components of the embodiments in the present disclosure generally described and shown in the drawings herein may be arranged and designed in a variety of different configurations.

Therefore, the following detailed description of the embodiments of the present disclosure provided in the drawings is not intended to limit the scope of the present disclosure claimed, but only represents chosen embodiments of the present disclosure. Based on the embodiments in the present disclosure, all of other embodiments obtained by those ordinarily skilled in the art without using any inventive efforts shall fall within the scope of protection of the present disclosure.

It should be noted that like reference signs and letters represent like items in the following drawings; therefore, once a certain item is defined in one drawing, it is not needed to be further defined or explained in subsequent drawings.

In the description of the present disclosure, it should be noted that orientation or positional relations indicated by the terms such as "center", "upper", "lower", "left", "right", "vertical", "horizontal", "inner", and "outer" are based on orientation or positional relations as shown in the drawings, or orientation or positional relations of a product of the present disclosure when being conventionally placed in use, merely for facilitating describing the present disclosure and simplifying the description, rather than indicating or implying that related devices or elements have to be in a specific orientation or configured and operated in a specific orientation; therefore, they should not be construed as limitation to the present disclosure. Besides, the terms "first", "second", "third", etc. are merely used for distinguishing the description, but should not be construed as indicating or implying importance in the relativity.

Moreover, the terms "horizontal", "vertical" and the like do not mean that parts are required to be absolutely horizontal or overhanging, but may be slightly inclined. For example, by "horizontal" it merely means that a structure is more horizontal in comparison with "vertical", rather than being completely horizontal, while the structure may be slightly inclined.

In the description of the present disclosure, it further should be noted that, unless otherwise specifically specified and defined, the terms "set", "mount", "link", and "connect" should be understood in a broad sense. For example, a connection may be a fixed connection, a detachable connection, or an integrated connection; it may be a mechanical connection or an electrical connection; it may be direct connection or indirect connection through an intermediary, and it also may be inner communication between two elements. For those ordinarily skilled in the art, specific meanings of the above terms in the present disclosure could be understood according to specific circumstances.

Compared with the existing three-arm clip, a three-arm clip provided in the present disclosure has the advantage of a simple structure, and may maintain a self-locking state between movable arms 120 and a fixed portion without providing an additional limiting elastic sheet.

Embodiment 1

Figure 2:
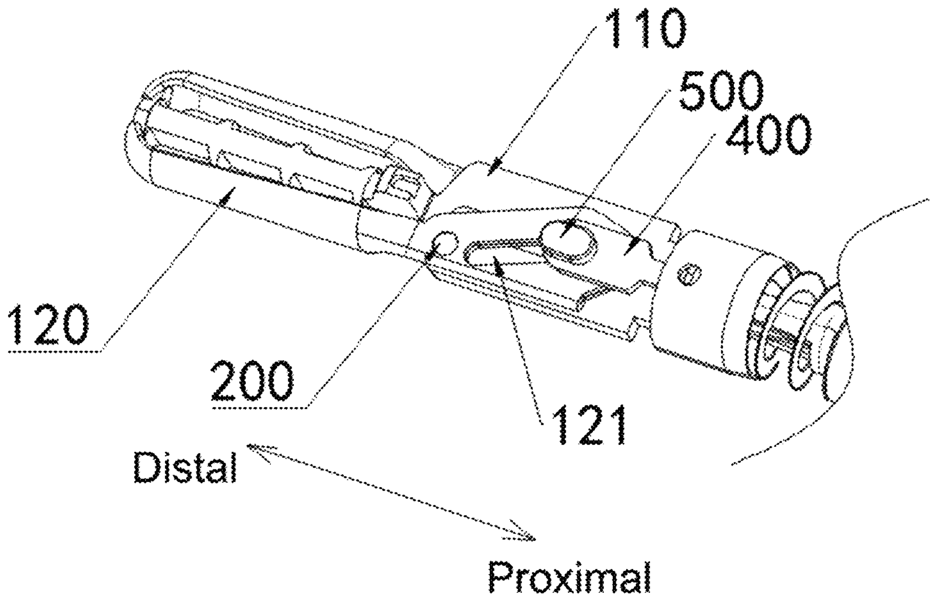
FIG. 2 is a schematic diagram of the three-arm clip in FIG. 1 after a cover on one side is removed.

A three-arm clip provided in the present disclosure includes a clamping component. The clamping component includes a fixed portion and two movable arms 120 rotationally connected to the fixed portion, wherein the movable arms 120 have a closed state, an open state and a self-locking state. When distal ends of the two movable arms 120 respectively approach to each other, they may be switched to the closed state, as shown in FIG. 1 and FIG. 2. On the contrary, when the distal ends of the two movable arms 120 respectively get away from each other, they may be switched to the open state, as shown in FIG. 4.

Figure 4:
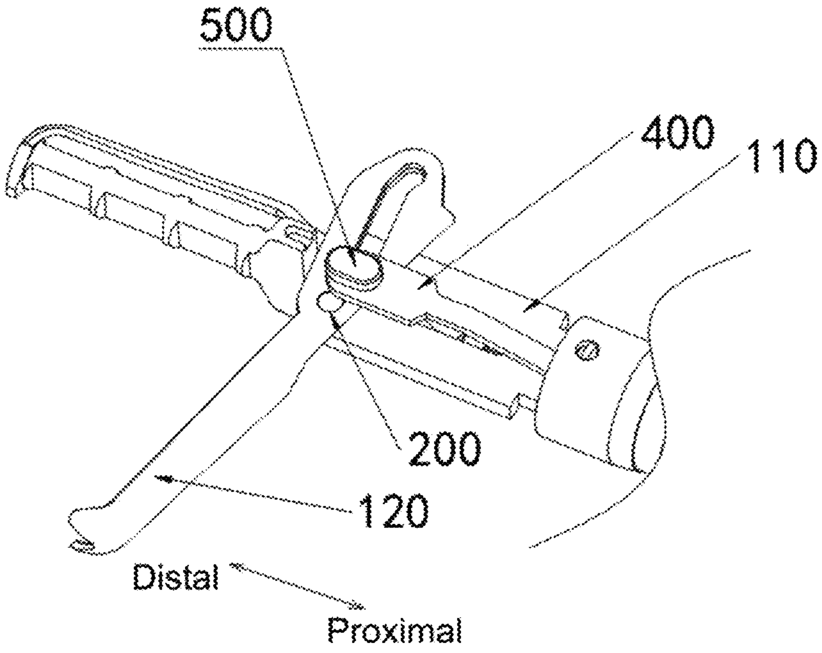
FIG. 4 is a schematic diagram of the three-arm clip in FIG. 2 after being opened.

As shown in FIG. 2 and FIG. 4, the clamping component further includes two sliding slot pins 500, wherein each sliding slot pin 500 is corresponding to one movable arm 120, and opening and closing of the movable arms 120 are realized through the sliding slot pins 500. Each of the movable arms 120 is provided with a first sliding slot 121, and the fixed portion is provided with a guiding slot 600 extending in a distal-proximal direction, wherein when the three-arm clip is in normal use, an end close to an operator is a proximal end, and an end far away from the operator is a distal end. As shown in FIG. 2, when the movable arms 120 are in the closed state, an extending direction of the first sliding slots 121 is inclined relative to an extending direction of the guiding slot 600. The sliding slot pins 500 are provided in the first sliding slots 121 and the guiding slot 600, and because the fixed portion is stationary during operation, the sliding slot pins 500 only slide along the extending direction of the guiding slot 600. By pushing the sliding slot pins 500 distally, the sliding slot pins 500 may be moved distally along the guiding slot 600. During movement, the sliding slot pins 500 push the inclined first sliding slots 121, so as to drive the movable arms 120 to rotate relative to the fixed portion, and the two movable arms 120 are turned to the open state, as shown in FIG. 4. On the contrary, by pushing the sliding slot pins 500 proximally, the two movable arms 120 may be turned to the closed state.

Figure 5:
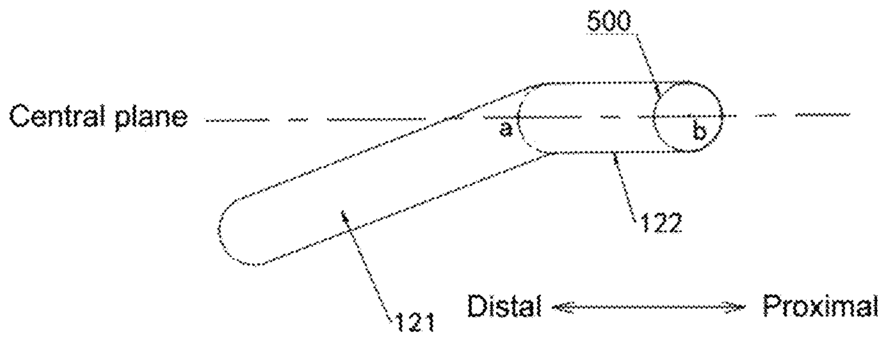
FIG. 5 is a diagram of self-locking principle of the three-arm clip provided in Embodiment 1 of the present disclosure.

As shown in FIG. 5, different from the three-arm clip in the prior art, the proximal ends of the first sliding slots 121 of the three-arm clip in the present embodiment are each connected with self-locking slots 122, and by pushing the sliding slot pins 500 proximally along the guiding slot 600, when the sliding slot pins 500 slide from the proximal ends of the first sliding slots 121 to proximal ends of the self-locking slots 122, the movable arms 120 are switched from the closed state to the self-locking state. The sliding slot pins 500 located in the self-locking slots 122 interact with the guiding slot 600, so as to form the self-locking, and without external force intervention, the movable arms 120 cannot be spread open solely by an expansion force of tissues clamped by the distal ends of the movable arms 120. In the present solution, by providing the self-locking slots 122 and realizing the self-locking between the movable arms 120 and the fixed portion in cooperation with the sliding slot pins 500, a snap-fitting structure such as a limiting elastic sheet may not be added to the movable arms 120, so that the three-arm clip has a reduced outer diameter, and may pass through an endoscope with a small working channel. Moreover, the structure is simplified and optimized, and difficulty of processing technology is reduced, so that production and quality costs are reduced, and good technology is popularized and applied.

When the movable arms 120 are in the self-locking state, axes b of the sliding slot pins 500 are located on a central plane of the guiding slot 600. In the above, it should be noted that the central plane is not an entity plane, but is a virtual auxiliary plane for convenience of describing the structure. A central line of the guiding slot 600 is located on the central plane, and an opening-closing direction of the movable arms 120 is perpendicular to the central plane.

Figure 6:
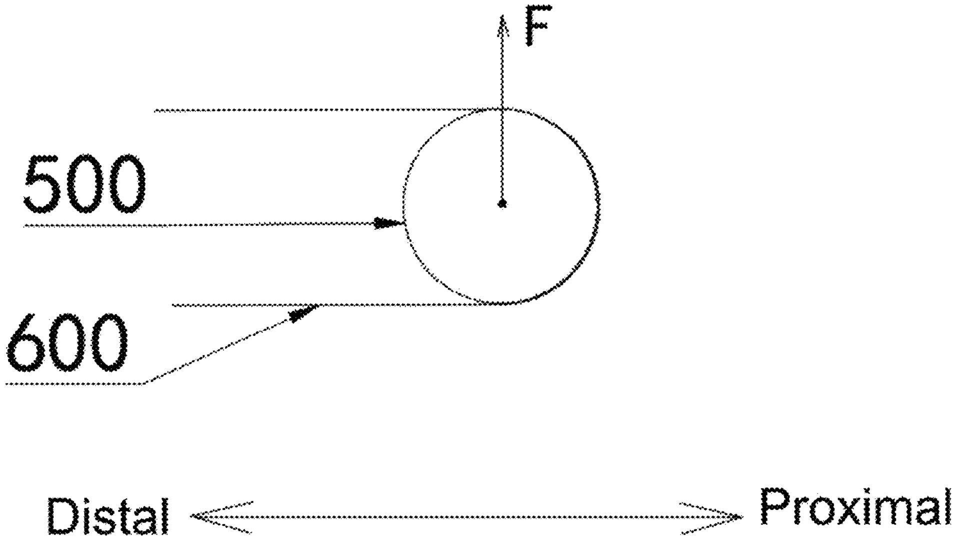
FIG. 6 is a force diagram of a sliding slot pin in FIG. 5.

In the present embodiment, as shown in FIG. 5, when the movable arms 120 are in the self-locking state, distal midpoints a of the self-locking slots 122 are located on the central plane, wherein the distal midpoints of the self-locking slots 122 refer to points in the middle of the distal ends of the self-locking slots 122 in a width direction. A connecting line between the point a and a point b in FIG. 5 is located on the central plane. When the two movable arms 120 are completely turned into the self-locking state, the sliding slot pins 500 are located at the proximal ends of the self-locking slots 122, and without external force intervention, the movable arms 120 cannot be spread open solely by the expansion force of the tissues clamped by the distal ends of the movable arms 120. As shown in FIG. 2, FIG. 5 and FIG. 6, because the movable arms 120 are in the self-locking state, when the distal ends of the movable arms 120 generate a certain expansion force, the movable arms 120 apply a pressure F to the sliding slot pins 500 through the self-locking slots 122. Since the connecting line between the point a and the point b is located on the central plane, the pressure applied to the sliding slot pins 500 is exactly perpendicular to the extending direction of the guiding slot 600, the pressure F has no component force in the extending direction of the guiding slot 600, so that there will be no displacement, and the sliding slot pins 500 will not move along the guiding slot 600, thereby realizing self-locking.

Figure 10:
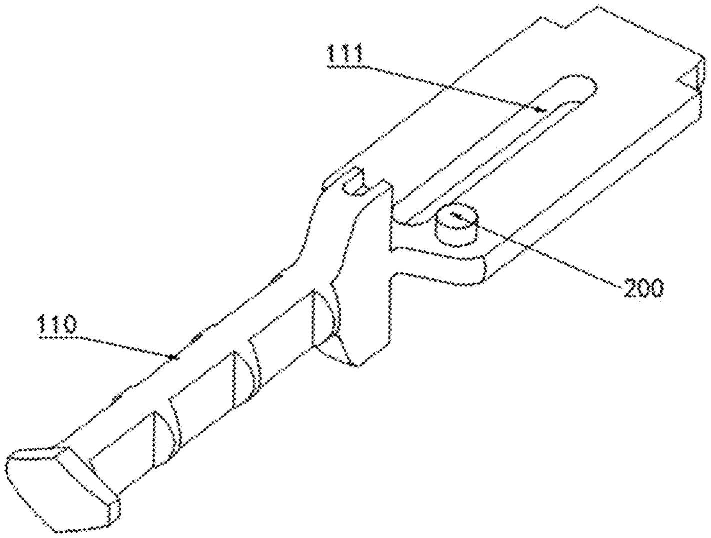
FIG. 10 is a schematic diagram of a fixed arm of the three-arm clip provided in Embodiment 1 of the present disclosure.

As shown in FIG. 1, FIG. 4 and FIG. 10, the fixed portion includes a fixed arm 110 extending in the distal-proximal direction, and the movable arms 120 are rotationally connected to the fixed arm 110 through shafts 200. In the present embodiment, an opening-closing direction of the two movable arms 120 may be a left-right direction, and the two movable arms 120 may be connected to the fixed arm 110 respectively from front and back side surfaces of the fixed portion, and a front-back direction is perpendicular to the left-right direction.

Figure 3:
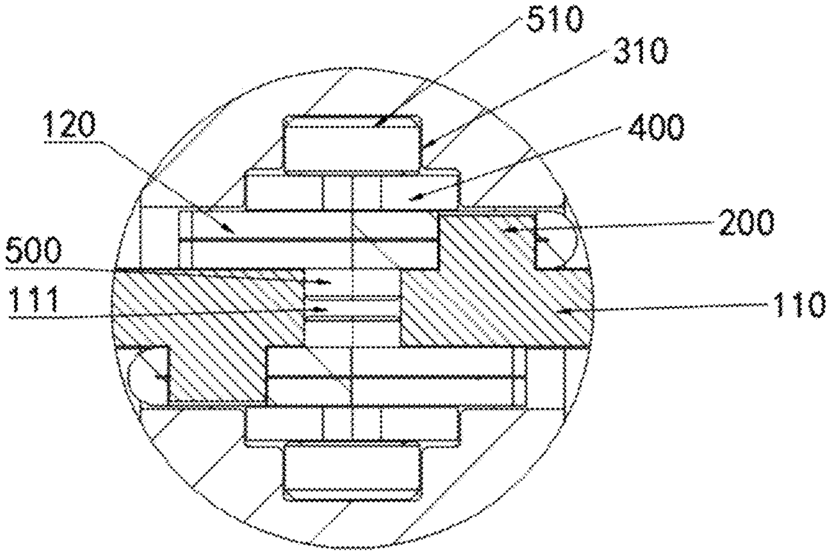
FIG. 3 is a sectional view along an A-A direction in FIG. 1.

Specifically, as shown in FIG. 2 to FIG. 4, two shafts 200 are respectively provided on left and right sides of the fixed arm 110, wherein one shaft 200 is located on a front surface of the fixed arm 110, and the other is provided on a back surface of the fixed arm 110, so that they are respectively rotationally connected to the two movable arms 120 located on the front and back surfaces of the fixed arm 110.

As shown in FIG. 3, the guiding slot 600 includes a second sliding slot 111 provided on the fixed arm 110, wherein the second sliding slot 111 runs through the front and back surfaces of the fixed arm 110 and extends in the distal-proximal direction, and tail ends of the sliding slot pins 500 corresponding to the two movable arms 120 extend into the second sliding slot 111 from front and back surfaces of the fixed arm 110. The second sliding slot 111 has an effect of guiding the tail ends of the sliding slot pins 500, so that the sliding slot pins 500 move in the distal-proximal direction.

As shown in FIG. 1, FIG. 3, FIG. 8 and FIG. 9, the fixed portion further includes two covers 300 extending from near to far. The two covers 300 are provided on the front and back surfaces of the fixed arm 110 and cover the two movable arms 120 on the front and back surfaces of the fixed arm 110, which may have a certain blocking effect on the movable arms 120. Meanwhile, the covers 300 further may withhold the movable arms 120, so as to fix the movable arms 120 between the fixed arm 110 and the covers 300, making the structure compact. In the above, the covers 300 and the fixed arm 110 may be integrally molded, or connected through a connection structure.

As shown in FIG. 3, the guiding slot 600 further may include third sliding slots 310 provided on surfaces of the covers 300 facing the fixed arm 110, wherein the third sliding slots 310 extend in the distal-proximal direction, and top ends of the sliding slot pins 500 are connected slidably in the third sliding slots 310. That is to say, lower ends of the sliding slot pins 500 are connected slidably in the second sliding slots 111, and upper ends are connected slidably in the third sliding slots 310, so that both upper and lower ends have a limiting effect, thereby preventing motion offset during sliding of the sliding slot pins 500. Moreover, the sliding slot pins 500 are in contact with the second sliding slots 111 and the third sliding slots 310 respectively, so that a friction force may be increased during the self-locking, thereby improving self-locking strength.

Further, as shown in FIG. 2, each sliding slot pin 500 is provided with a cap 510 on a top portion, and the cap 510 is located in the third sliding slot 310. The cap 510 may be in a waist shape. The cap 510 has a first guiding surface and a second guiding surface on two opposite sides, and the first guiding surface and the second guiding surface are respectively in sliding contact with two opposite slot walls of the third sliding slot 310. A contact area is increased by increasing the first guiding surface and the second guiding surface, thereby further increasing the friction force. Moreover, the cap 510 is in contact with a bottom surface of the third sliding slot 310, which may avoid rotation of the tail end of the sliding slot pin 500 towards one side of the cover 300.

The three-arm clip further includes releasing members 400. Each of the releasing members 400 may be located at one side of the movable arm 120 facing back to the fixed arm 110. The releasing members 400 are detachably connected to the sliding slot pins 500. In an initial state, the movable arms 120 are in the open state, the releasing members 400 are connected to the sliding slot pins 500. After clamping is completed, the releasing members 400 are dragged with force, so that the releasing members 400 may be detached from the sliding slot pins 500. The releasing members 400 can drive the sliding slot pins 500 to move in the distal-proximal direction, and the operator pushes and pulls the sliding slot pins 500 through the releasing members 400, so that the movable arms 120 rotate around the shafts 200 and perform opening and closing actions relative to the fixed arm 110 and form the self-locking.

In the present embodiment, as shown in FIG. 4, the movable arms 120 are provided with holes, wherein depth of the holes is greater than or equal to height of the shafts 200, so that top ends of the shafts 200 are lower than or flush with outer side surfaces of corresponding movable arms 120. That is to say, top portions of the shafts 200 do not protrude from the holes, and do not interfere with the releasing members 400 moving linearly.

The operator may push the releasing members 400 distally, so that the sliding slot pins 500 move distally in the distal-proximal direction. The first sliding slots 121 are pushed by the sliding slot pins 500, the movable arms 120 rotate around the shafts 200, and included angles between the movable arms 120 and the fixed arm 110 are increased. Because the top portions of the shafts 200 are lower than the holes in the present solution, that is to say, the shafts 200 do not protrude from outer side walls of the movable arms 120, the releasing members 400, when moving distally along the outer side walls of the movable arms 120, will not be interfered by the shafts 200, and thus may move distally farther. As the sliding slot pins 500 continue to move distally, an opening angle of the movable arms 120 also becomes larger and larger. Compared with the three-arm clip in the prior art, the three-arm clip provided in the present disclosure has a larger opening angle. Compared with the prior art, the movable arms may render the same clamping effect in a case of being relatively short, and may satisfy more surgical scenes. Moreover, it should be noted that as shown in FIG. 3, in the present solution, at least part of inward projections of profiles of motion paths of the releasing members 400 falls within the holes. That is to say, in the solution, distances between the movable arms 120, the shafts 200 and the releasing members 400 are very small, and thus the structure is compact, which also greatly reduces a diameter of the three-arm clip, wherein when the three-arm clip is in the closed state, a value range of a maximum outer diameter thereof may be 2.3 mm-2.9 mm.

Being not affected by the shafts 200, the farthest ends of movement paths of the releasing members 400 go beyond positions where the shafts 200 are located, so that the opening angles between the movable arms 120 and the fixed arm 110 may be greater than 90, thereby achieving the purpose of large-range clamping.

Figure 7:
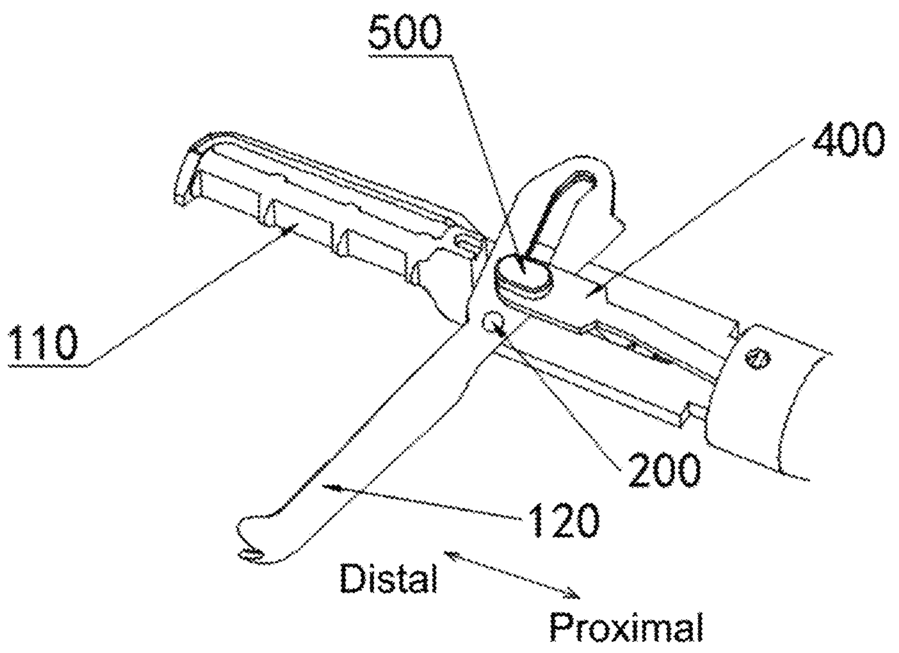
FIG. 7 is a schematic diagram of another three-arm clip provided in Embodiment 1 of the present disclosure after a cover on one side is removed.
Figure 8:
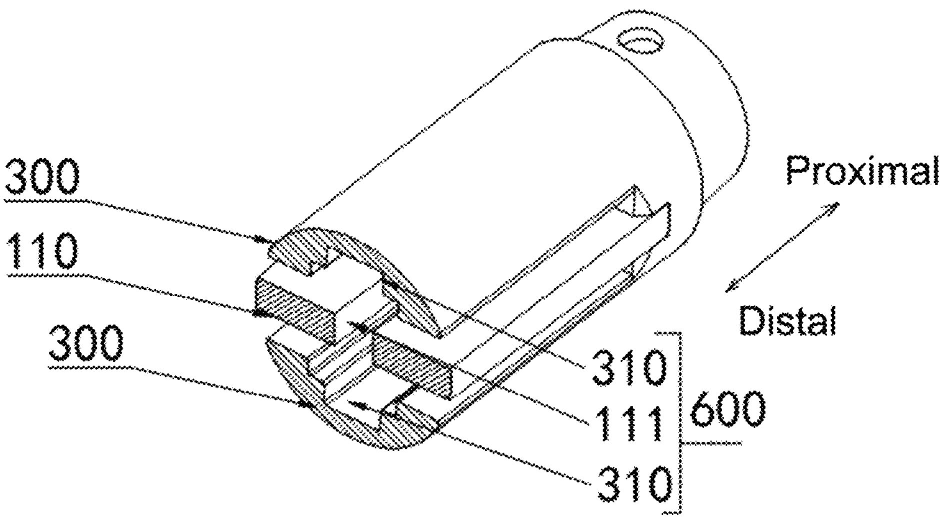
FIG. 8 is a sectional view of a fixed portion of the three-arm clip provided in Embodiment 1 of the present disclosure.
Figure 9:
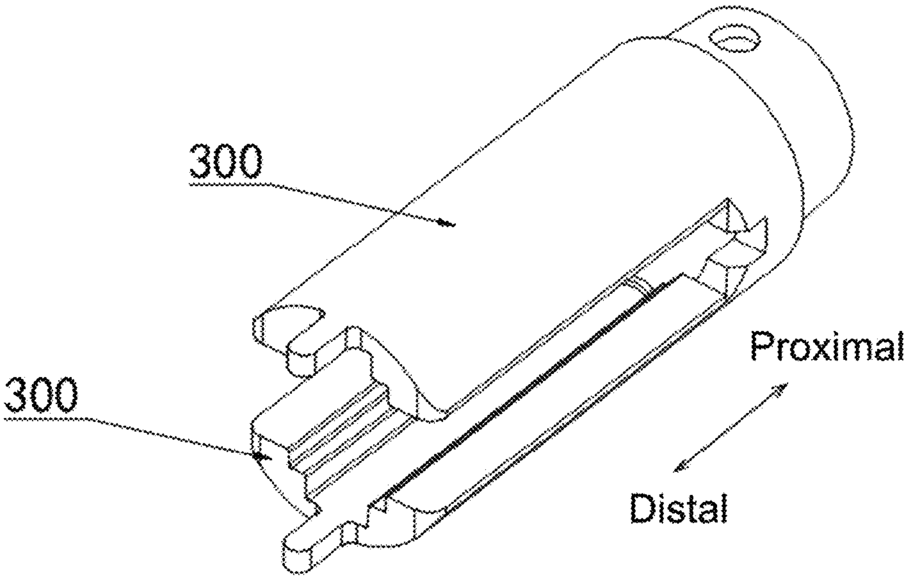
FIG. 9 is a schematic diagram of covers of the three-arm clip provided in Embodiment 1 of the present disclosure.

In an implementable mode, as shown in FIG. 7, in order to prevent the releasing members 400 from interference with the shafts 200 during pushing and pulling, the shafts 200 also may be provided outside the movement paths of the releasing members 400. In this embodiment, the two shafts are respectively located at two left and right sides of the releasing members, that is to say, width of a gap between the two shafts 200 is greater than width of the releasing members 400.

In the present embodiment, the shafts 200 are integrally molded with the fixed arm 110.

Embodiment 2

Figure 11:
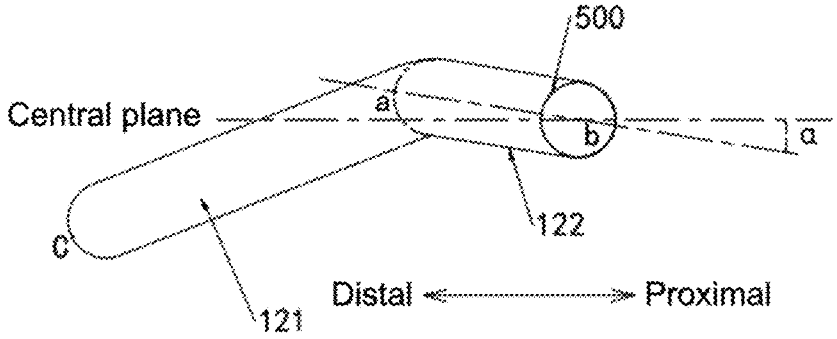
FIG. 11 is a diagram of self-locking principle of a three-arm clip provided in Embodiment 2 of the present disclosure.

Embodiment 2 is the same as Embodiment 1 in that when the movable arms 120 are in the self-locking state, the distal midpoints of the self-locking slots 122 are located on the central plane. Embodiment 2 is different from Embodiment 1 is that, as shown in FIG. 11, in the present embodiment, the distal midpoints of the self-locking slots 122 and distal midpoints c of the first sliding slots 121 are located on two opposite sides of the central plane, respectively, wherein the distal midpoints c of the first sliding slots 121 refer to points in the middle of the distal ends of the first sliding slots 121 in a width direction. As shown in FIG. 11, the point b is located on the central plane, the point c and the point a are respectively located on two sides of the central plane, the extending direction of the self-locking slot 122 is inclined relative to the extending direction of the guiding slot, and an inclination angle is α.

Figure 12:
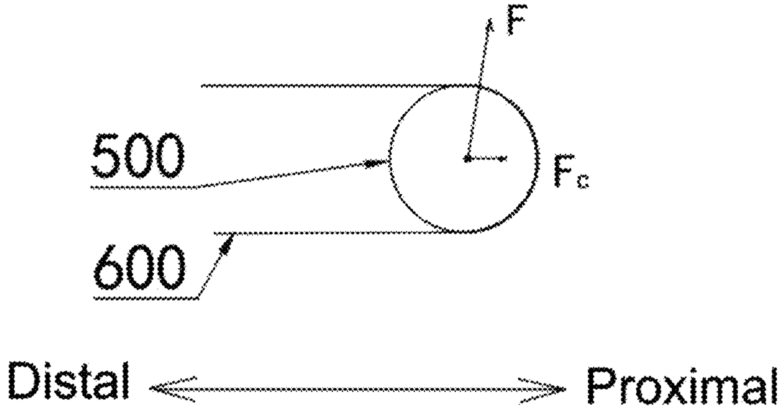
FIG. 12 is a force diagram of a sliding slot pin in FIG. 11.

As shown in FIG. 11 and FIG. 12, when the distal ends of the movable arms 120 generate a certain expansion force, the movable arms 120 apply the pressure F to the sliding slot pins 500 through the self-locking slots 122, and because the extending direction of the self-locking slots 122 in this case have the inclination angle α relative to the central plane, the sliding slot pins 500 located in the self-locking slots 122 will be subjected to the pressure F inclined towards the proximal ends, and in this case the pressure F on the sliding slot pins 500 has a component force $F_c$ towards the proximal ends. In this situation, the greater the expansion force of the distal ends of the movable arms 120 is, the tighter the self-locking is.

Embodiment 3

Figure 13:
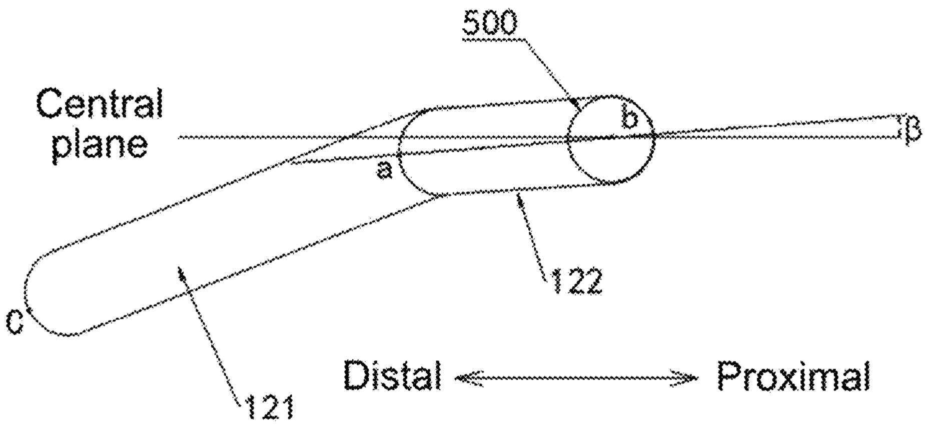
FIG. 13 is a diagram of self-locking principle of a three-arm clip provided in Embodiment 3 of the present disclosure.

Embodiment 3 is the same as Embodiment 2 in that when the movable arms 120 are in the self-locking state, the distal midpoints of the self-locking slots 122 are located on the central plane. Embodiment 3 is different from Embodiment 2 in that an inclination direction of the self-locking slots 122 is different. Specifically, as shown in FIG. 13, the distal midpoints a of the self-locking slots 122 and the distal midpoints c of the first sliding slots 121 are located on the same side of the central plane, and an included angle β between a connecting line between the distal midpoint a of the self-locking slot 122 and the axis b of the sliding slot pin 500 and the central plane is within a preset self-locking angle range. The point b is located on the central plane, the point c and the point a are respectively located on the same side of the central plane, the extending direction of the self-locking slot 122 is inclined relative to the extending direction of the guiding slot, and an inclination angle is β.

Figure 14:
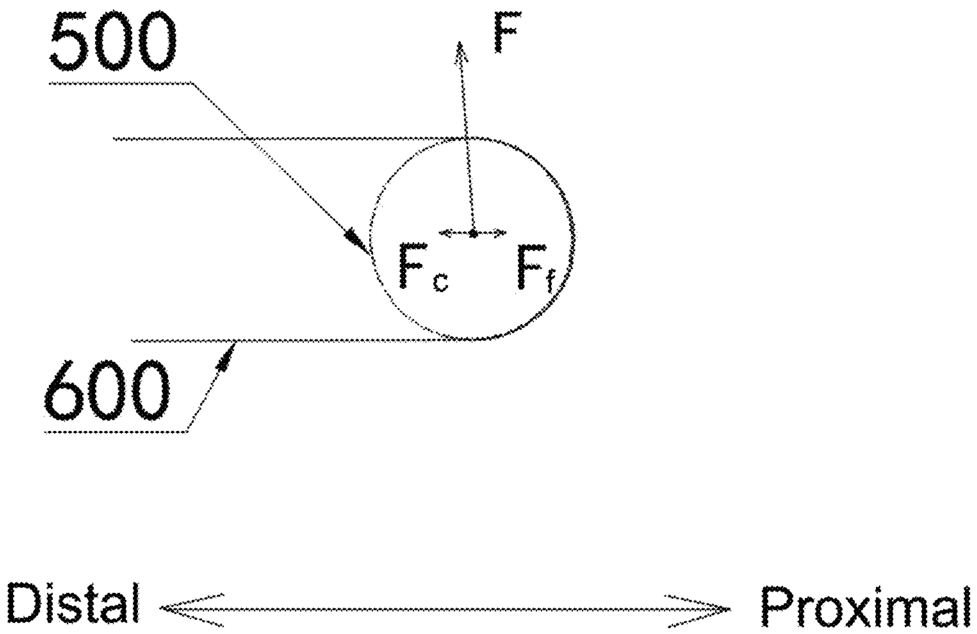
FIG. 14 is a force diagram of a sliding slot pin in FIG. 13.

As shown in FIG. 13 and FIG. 14, when the distal ends of the movable arms 120 generate a certain expansion force, the movable arms 120 apply the pressure F to the sliding slot pins 500 through the self-locking slots 122. Because the extending direction of the self-locking slots 122 in this case have the inclination angle β relative to the central plane, the sliding slot pins 500 located in the self-locking slots 122 will be subjected to the pressure F inclined towards the distal ends, and in this case the pressure F on the sliding slot pins 500 has a component force Fe towards the distal ends. However, since the inclination angle β satisfies a preset self-locking angle, that is, does not exceed a self-locking critical value, the above component force Fe may be offset by a friction force Fr between the sliding slot pins 500 and the guiding slot 600, so that the sliding slot pins 500 are relatively stationary, and the self-locking between the movable arms 120 and the fixed arm 110 is realized.

In the above, a value range of the preset self-locking angle is related to a material of a product, and the material will affect a friction coefficient. Calculation of the preset self-locking angle belongs to the prior art in the field of mechanical analysis.

Specifically, materials of the movable arms 120, the fixed portion and the sliding slot pins 500 may be stainless steel, and the value range of the preset self-locking angle β may be 0-8°.

To sum up, in the present solution, by providing the self-locking slots 122 and realizing the self-locking between the movable arms 120 and the fixed portion in cooperation with the sliding slot pins 500, a snap-fitting structure such as a limiting elastic sheet may not be provided on the movable arms 120, so that a product structure is simpler, manufacture is convenient, and production costs and product weight are reduced.

Moreover, a mode of providing the shafts 200 is improved in the solution, that is, an exposed manner in the prior art is modified into a hidden manner disclosed in the present solution; therefore, the outer diameter of the three-arm clip can be reduced, and the problem that the shafts 200 interfere with the movement of the releasing members 400 is not caused after the reduction.

Finally, it should be noted that the above embodiments are only used to illustrate the technical solutions of the present disclosure, and not to limit the present disclosure. Although the present disclosure has been described in detail with reference to the foregoing embodiments, those ordinarily skilled in the art should understand that they still could modify the technical solutions described in the foregoing embodiments, or equivalently replace some or all of the technical features therein. These modifications or replacements do not make the essence of corresponding technical solutions deviate from the scope of the technical solutions of the embodiments of the present disclosure.

What is claimed is:

1. A three-arm clip, comprising a clamping component, wherein the clamping component comprises a fixed portion and two movable arms rotationally connected to the fixed portion, and the movable arms have an open state, a closed state and a self-locking state;

the clamping component further comprises two sliding slot pins, each of the movable arms is provided with a first sliding slot, the fixed portion is provided with a guiding slot extending in a distal-proximal direction, wherein when the movable arms are in the closed state, an extending direction of the first sliding slot is inclined relative to an extending direction of the guiding slot; each of the sliding slot pins is provided in the first sliding slot and the guiding slot, and along the guiding slot, by driving the sliding slot pins, the movable arms can be driven to be switched between the closed state and the open state; and each of the movable arms is provided with a self-locking slot, a distal end of the self-locking slot communicates with a proximal end of the first sliding slot; and along the guiding slot, when each of the sliding slot pins slides from the proximal end of the first sliding slot to a proximal end of the self-locking slot, the movable arm is switched from the closed state to the self-locking state;

wherein the fixed portion comprises a fixed arm extending in the distal-proximal direction, the fixed arm is provided with shafts, and each of the movable arms is provided with a hole connected with the shaft, and each of the movable arms is rotationally connected to the fixed arm through the shaft;

the three-arm clip further comprises releasing members, wherein each of the releasing members is detachably connected to the sliding slot pin, and each of the releasing members is capable of driving the sliding slot pin to move along the guiding slot, so that the sliding slot pin moves in the first sliding slot and the self-locking slot; and a depth of the hole is greater than or equal to a height of the shaft, so that a top end of the shaft is lower than or flush with an outer side surface of the movable arm, so as to prevent the shaft from interfering with movement of the releasing member.

2. The three-arm clip according to claim 1, wherein when each of the movable arms is in the self-locking state, an axis b of the sliding slot pin is located on a central plane of the guiding slot, wherein a central line of the guiding slot is located on the central plane, and an opening-closing direction of each of the movable arms is perpendicular to the central plane;

when each of the movable arm is in the self-locking state, a distal midpoint a of the self-locking slot is located on the central plane; or a distal midpoint a of the self-locking slot and a distal midpoint c of the first sliding slot are located on two opposite sides of the central plane, respectively; or the distal midpoint a of the self-locking slot and the distal midpoint c of the first sliding slot are located on the same side of the central plane, and an included angle β between a connecting line between the distal midpoint a of the self-locking slot and the axis b of the sliding slot pin and the central plane is within a preset self-locking angle range; and each of the sliding slot pins is located in the self-locking slot and makes the movable arms maintain the self-locking state relative to the fixed portion through the guiding slot.

3. The three-arm clip according to claim 2, wherein when each of the movable arms is in the self-locking state, the distal midpoint a of the self-locking slot and the distal midpoint c of the first sliding slot are located on the same side of the central plane, and the included angle β between the connecting line between the distal midpoint a of the self-locking slot and the axis b of the sliding slot pin and the central plane is within a preset self-locking angle range; and a value range of the preset self-locking angle β is 0-8°.

4. The three-arm clip according to claim 1, wherein the fixed portion comprises a fixed arm extending in the distal-proximal direction, and each of the movable arms is rotationally connected to the fixed arm; and the guiding slot comprises a second sliding slot provided on the fixed arm, wherein the second sliding slot runs through each side of the fixed arm, and tail ends of the sliding slot pins corresponding to the two movable arms extend into the second sliding slot from each side of the fixed arm respectively.

5. The three-arm clip according to claim 1, wherein the fixed portion comprises a fixed arm extending in the distal-proximal direction, and each of the movable arms is rotationally connected to the fixed arm;

the fixed portion further comprises two covers extending a proximal end to a distal end, the two covers are provided on each side of the fixed arm and cover at least part of the two movable arms rotatably set on each side of the fixed arm; and the guiding slot comprises a third sliding slot provided on a surface of each of the covers facing the fixed arm, and a top end of each of the sliding slot pins is connected slidably in the third sliding slot.

6. The three-arm clip according to claim 5, wherein each of the sliding slot pins is provided with a cap on a top portion, and the cap is slidably provided in the third sliding slot; and the cap has a first guiding surface and a second guiding surface on two opposite sides, and the first guiding surface and the second guiding surface are respectively in sliding contact with two opposite slot walls of the third sliding slot.

7. The three-arm clip according to claim 1, wherein the fixed portion comprises a fixed arm extending in the distal-proximal direction, the fixed arm is provided with shafts, and the movable arms are rotationally connected to the fixed arm through the shafts;

the three-arm clip further comprises releasing members, wherein each of the releasing members is detachably connected to the sliding slot pin, and each of the releasing members is capable of driving the sliding slot pin to move along the guiding slot, so that the sliding slot pin moves in the first sliding slot and the self-locking slot; and each of the shafts is located outside a movement path of the releasing member.

8. The three-arm clip according to claim 1, wherein at least a portion of a projection of a motion path profile of each of the releasing members towards the movable arm falls within the hole.

9. The three-arm clip according to claim 8, wherein when the three-arm clip is in the closed state, a value range of a maximum outer diameter thereof is 2.3 mm-2.9 mm.

10. The three-arm clip according to claim 7, wherein the farthest end of a movement path of each of the releasing members goes beyond a position where the shaft is located.

11. The three-arm clip according to claim 4, wherein the fixed portion comprises a fixed arm extending in the distal-proximal direction, and each of the movable arms is rotationally connected to the fixed arm;

the fixed portion further comprises two covers extending from a proximal end to a distal end, the two covers are provided on each side of the fixed arm and cover at least part of the two movable arms on each side of the fixed arm; and the guiding slot comprises a third sliding slot provided on a surface of each of the covers facing the fixed arm, and a top end of each of the sliding slot pins is connected slidably in the third sliding slot.

12. The three-arm clip according to claim 1, wherein the farthest end of a movement path of each of the releasing members goes beyond a position where the shaft is located.

13. A three-arm clip, comprising a clamping component, wherein the clamping component comprises a fixed portion and two movable arms rotationally connected to the fixed portion, and the movable arms have an open state, a closed state and a self-locking state;

the clamping component further comprises two sliding slot pins, each of the movable arms is provided with a first sliding slot, the fixed portion is provided with a guiding slot extending in a distal-proximal direction, wherein when the movable arms are in the closed state, an extending direction of the first sliding slot is inclined relative to an extending direction of the guiding slot; each of the sliding slot pins is provided in the first sliding slot and the guiding slot, and along the guiding slot, by driving the sliding slot pins, the movable arms can be driven to be switched between the closed state and the open state; and each of the movable arms is provided with a self-locking slot, a distal end of the self-locking slot communicates with a proximal end of the first sliding slot; and along the guiding slot, when each of the sliding slot pins slides from the proximal end of the first sliding slot to a proximal end of the self-locking slot, the movable arm is switched from the closed state to the self-locking state;

wherein the fixed portion comprises a fixed arm extending in the distal-proximal direction, and each of the movable arms is rotationally connected to the fixed arm;

the fixed portion further comprises two covers extending from a proximal end to a distal end, the two covers are provided on each side of the fixed arm and cover at least part of the two movable arms rotatably set on each side of the fixed arm;

the guiding slot comprises a third sliding slot provided on a surface of each of the covers facing the fixed arm, and a top end of each of the sliding slot pins is connected slidably in the third sliding slot; and wherein each of the sliding slot pins is provided with a cap on a top portion, and the cap is slidably provided in the third sliding slot; and the cap has a first guiding surface and a second guiding surface on two opposite sides, and the first guiding surface and the second guiding surface are respectively in sliding contact with two opposite slot walls of the third sliding slot.

* * * * *